(12) United States Patent
Hanson et al.

(10) Patent No.: US 9,807,951 B2
(45) Date of Patent: Nov. 7, 2017

(54) COMPOSITIONS ASSOCIATED WITH SOYBEAN REPRODUCTIVE GROWTH AND METHODS OF USE

(71) Applicant: PIONEER HI-BRED INTERNATIONAL, INC., Johnston, IA (US)

(72) Inventors: Sara Elizabeth Hanson, Wesley, IA (US); Leslie Charles Kuhlman, Lawrence, KS (US); Donald Kyle, Princeton, IL (US); Landon Linn Ries, Armstrong, IA (US); Jordan Spear, Algona, IA (US); John Bryan Woodward, Ankeny, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 15/125,738

(22) PCT Filed: Mar. 11, 2015

(86) PCT No.: PCT/US2015/019917
§ 371 (c)(1),
(2) Date: Sep. 13, 2016

(87) PCT Pub. No.: WO2015/179004
PCT Pub. Date: Nov. 26, 2015

(65) Prior Publication Data
US 2017/0027122 A1 Feb. 2, 2017

Related U.S. Application Data

(60) Provisional application No. 61/952,526, filed on Mar. 13, 2014.

(51) Int. Cl.
*A01H 1/04* (2006.01)
*C12Q 1/68* (2006.01)
*A01H 1/02* (2006.01)

(52) U.S. Cl.
CPC ............... *A01H 1/04* (2013.01); *A01H 1/02* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,455,758 B1 | 9/2002 | Johnson |
| 8,329,982 B2 | 12/2012 | Kyle et al. |
| 8,847,006 B2 | 9/2014 | Jenkinson et al. |
| 2008/0256660 A1 | 10/2008 | Jenkinson et al. |
| 2010/0122372 A1 | 5/2010 | Sebastian et al. |
| 2011/0191893 A1 | 8/2011 | Harada et al. |
| 2012/0324598 A1 | 12/2012 | Lu et al. |

FOREIGN PATENT DOCUMENTS

WO 2014/149920 A1 9/2014

OTHER PUBLICATIONS

Xia et al. (PNAS, (2012), pp. E2155-E2164).*
Tsuborkura et al. (Annals of Botany, (2013), pp. 1-13).*
Watanabe (Genetics 182: pp. 1251-1262 (Aug. 2009)).*
Lirui Cheng et al., Genetic analysis and QTL detection of reproductive period and post-flowering photoperiod responses in soybean, Theor Appl Genet, 2011, pp. 421-429, vol. 123.
Elroy R. Cober et al., Regulation of seed yield and agronomic characters by photoperiod sensitivity and growth habit genes in soybean, Theor Appl Genet, 2010, pp. 1005-1012, vol. 120.
Elroy R. Cober et al., A New Locus for Early Maturity in Soybean, Crop Science, Mar.-Apr. 2010, pp. 524-527, vol. 50.
R. H. Ellis et al., Effects of Photoperiod and Maturity Genes on Plant Growth, Partitioning, Radiation Use Efficiency, and Yield in Soyabean [*Glycine max* (L.) Merrill] 'Clark', Annals of Botany, 2000, pp. 335-343, vol. 85.
Larry Heatherly, Soybean maturity group, planting date and development related, Delta Farm Press, Oct. 14, 2005, 2 pages.
David L. Holshouser, Days to Soybean Physiological Maturity, Virginia Cooperative Extension, VirginiaTech, 2010, 1 page.
Kunihiko Komatsu et al., Identification of QTL controlling post-flowering period in soybean, Breeding Science, 2012, pp. 646-652, vol. 61, No. 5.
Saratha V. Kumudini et al., Photoperiod and E-genes Influence the Duration of the Reproductive Phase in Soybean, Crop Science, Jul.-Aug. 2007, pp. 1510-1517, vol. 47.
Chad D. Lee et al., Predicting Soybean First Flowering Date, UK Cooperative Extension Service, University of Kentucky—College of Agriculture, Mar. 2005, AGR 184, 2 pages.
Wenxin Li et al., QTL Mapping for Major Agronomic Traits across Two Years in Soybean (*Glycine max* L. Merr.), J. Crop Sci. Biotech., Sep. 2008, pp. 171-190, vol. 11 (3).
Weixian Liu et al., QTL identification of flowering time at three different latitudes reveals homeologous genomic regions that control flowering in soybean, Theor Appl Genet, 2011, pp. 545-553, vol. 123.
L. M. Mansur et al., Interval mapping of quantitative trait loci for reproductive morphological and seed traits of soybean (*Glycine max* L.), Theoretical and Applied Genetics, 1993, pp. 907-913, vol. 86, Issue 8.

(Continued)

*Primary Examiner* — Brent Page
*Assistant Examiner* — Jared Shapiro

(57) ABSTRACT

Molecular markers associated with soybean reproductive stage, methods of their use, and compositions having one or more marker loci are provided. Methods comprise detecting at least one marker locus, detecting a haplotype, and/or detecting a marker profile. Methods may further comprise crossing a selected soybean plant with a second soybean plant. Isolated polynucleotides, primers, probes, kits, systems, etc., are also provided, as well as plants and seeds comprising one or more marker loci and having a preferred reproductive growth phenotype.

12 Claims, No Drawings

(56) References Cited

OTHER PUBLICATIONS

Hisakazu Matsumura et al., AFLP Mapping of Soybean Maturity Gene E4, Journal of Heredity, 2008, pp. 193-197, vol. 99(2).

D. A. McWilliams et al., Soybean Growth and Management Quick Guide, North Dakota State University Extension Service, Jun. 1999, pp. 1-8.

C. D. Messina et al., A Gene-Based Model to Simulate Soybean Development and Yield Responses to Environment, Crop Science, 2006, pp. 456-466, vol. 46.

Stephen J. Molnar et al., Simple sequence repeat (SSR) markers linked to E1, E3, E4, and E7 maturity genes in soybean, Genome, 2003, pp. 1024-1036, vol. 46.

Praveen K. Pallikonda, Impact of E-genes on Soybean (*Glycine max* L. [Merr]) Development, Senescence and Yield, University of Kentucky Master's Theses, Paper 413, 2006, pp. 1-140.

V. E. Rozenzweig et al., Prospects of exploiting of photoperiod sensitivity gene $E_7$ in early soybean breeding and revealing of its sources with SSR-markers, Soybean Genetics Newsletter, 2008, No. 35, pp. 1-7, ref.17.

I. M. Tasma et al., Mapping genetic loci for flowering time, maturity, and photoperiod insensitivity in soybean, Molecular Breeding, 2001, pp. 25-35, vol. 8.

D. Wang et al., Identification of putative QTL that underlie yield in interspecific soybean backcross populations, Theor Appl Genet, 2004, pp. 458-467, vol. 108.

Jin Hee Shin et al., Molecular markers for the E2 and E3 genes controlling flowering and maturity in soybean, Mol. Breeding, 2012, pp. 1793-1798, vol. 30.

Q. J. Song et al., A new integrated genetic linkage map of the soybean, Theor Appl Genet, 2004, pp. 122-128, vol. 109.

R. J. Summerfield et al., Characterization of the Photoperiodic Response of Post-flowering Development in Maturity Isolines of Soyabean [*Glycine max* (L.) Merrill] 'Clark', Annals of Botany, 1998, pp. 765-771, vol. 82.

Yasutaka Tsubokura et al., Natural variation in the genes responsible for maturity loci E1, E2, E3 and E4 in soybean, Annals of Botany, 2013, pp. 1-13.

Satoshi Watanabe et al., Map-Based Cloning of the Gene Associated With the Soybean Maturity Locus E3, Genetics, Aug. 2009, pp. 1251-1262, vol. 182.

Satoshi Watanabe et al., A Map-Based Cloning Strategy Employing a Residual Heterozygous Line Reveals that the GIGANTEA Gene is Involved in Soybean Maturity and Flowering, Genetics, Jun. 2011, pp. 395-407, vol. 188.

Satoshi Watanabe et al., Genetic and molecular bases of photoperiod responses of flowering in soybean, Breeding Science, 2012, pp. 531-543, vol. 61.

Zhengjun Xia et al., Positional cloning and characterization reveal the molecular basis for soybean maturity locus E1 that regulates photoperiodic flowering, PNAS, Published May 22, 2012, E2155-2164.

Zhengjun Xia et al., Molecular identification of genes controlling flowering time, maturity, and photoperiod response in soybean, Plant Syst Evol., 2012, pp. 1217-1227, vol. 298.

Da-Wei Xin et al., Analysis of quantitative trait loci underlying the period of reproductive growth in soybean (*Glycine max* [L.] Merr.), Euphytica, 2008, pp. 155-165, vol. 162.

Meilan Xu et al., Genetic variation in four maturity genes affects photoperiod insensitivity and PHYA-regulated post-flowering responses of soybean, BMC Plant Biology, 2013, p. 91, vol. 13.

Tetsuya Yamada et al., Effects on flowering and seed yield of dominant alleles at maturity loci E2 and E3 in a Japanese cultivar, Enrei, Breeding Sciences, 2012, pp. 653-660, vol. 61.

Naoki Yamanaka et al., An Informative Linkage Map of Soybean Reveals QTLs for Flowering Time, Leaflet Morphology and Regions of Segregation Distortion, DNA Research, 2001, pp. 61-72, vol. 8.

U.S. Appl. No. 14/776,044, filed Sep. 14, 2015.

International Search Report and Written Opinion—PCT/US2015/019917—dated Nov. 20, 2015.

International Search Report and Written Opinion—PCT/US2014/021517—dated Jun. 2, 2014.

\* cited by examiner

COMPOSITIONS ASSOCIATED WITH SOYBEAN REPRODUCTIVE GROWTH AND METHODS OF USE

FIELD OF THE INVENTION

This invention relates to compositions associated with reproductive stage in soybean plants and methods of their use.

BACKGROUND

Soybeans (*Glycine max* L. Merr.) are a major cash crop and investment commodity in North America and elsewhere. Soybean is the world's primary source of seed oil and seed protein. Improving soybean adaptation for various growing regions and environmental conditions is crucial for maximizing yields.

There remains a need for means to identify genomic regions associated with reproductive stages in soybean plants. The compositions and methods provide important tools for use in plant breeding programs to optimize or maximize the reproductive growth stage, and/or to develop varieties adapted for various growing regions or environments.

SUMMARY

Molecular markers associated with soybean reproductive stages, methods of their use, and compositions having one or more marker loci are provided. Methods comprise detecting at least one marker locus, detecting a haplotype, and/or detecting a marker profile. Methods may further comprise crossing a selected soybean plant with a second soybean plant. Isolated polynucleotides, primers, probes, kits, systems, etc., are also provided, as well as plants and seeds comprising one or more marker loci and having a preferred reproductive growth phenotype.

SUMMARY OF SEQUENCES

SEQ ID NOs: 1-15 comprise nucleotide sequences of regions of the soybean genome, each capable of being used as a probe or primer, either alone or in combination, for the detection of a marker locus associated with reproductive growth in soybean. In certain examples, Primer1 and Primer2 are used as allele specific primers and Probe1 and Probe2 are used as allele probes. The SEQ ID NOs provided in the "Region" column of the table below are each a genomic DNA region encompassing the respective marker locus. In some examples, the primers and/or probes detect the polymorphism based on a polynucleotide complementary to the genomic region provided here. It is to be understood that the sequences provided are sufficient for one of skill in the art to detect a locus associated with reproductive growth in soybean regardless of the orientation (forward, or reverse) of the strand used for detection.

| Locus | Primer 1 SEQ ID NO: | Primer 2 SEQ ID NO: | Probe 1 SEQ ID NO: | Probe 2 SEQ ID NO: | Region SEQ ID NO: |
|---|---|---|---|---|---|
| S03703-1 | 1 | 2 | 3 | 4 | 5 |
| S16601-001 | 6 | 7 | 8 | 9 | 10 |
| S01574-1 | 11 | 12 | 13 | 14 | 15 |

DETAILED DESCRIPTION

The timing of soybean flowering and maturity are important agronomical traits that are associated with yield. These traits are largely affected by the genetic response to environmental signals such as day-length and temperature. Through selective breeding for flowering and maturity phenotypes, soybean varieties have been developed that are ideally suited for maximizing yield within a particular environment. Field testing for reproductive characteristics is laborious and challenging, and it cannot be accomplished until late in the plant life cycle. Having markers that can be used to select for reproductive growth expedite the introgression of desired alleles into elite cultivars.

Multiple genetic loci have been identified as containing genes that control the reproductive growth period of soybean. Relative maturity (RM) in soybean plays a significant role in determining final seed yield, and it is common for seed yield and the length of reproductive growth to have a positive correlation. Extending the reproductive period through manipulation of these loci is important for maximizing yield potential. However, it is important to evaluate soybean varieties in the correct environments. Utilizing markers associated with soybean reproductive growth that distinguish between early and late alleles, such as early and late alleles for initiation of flowering, provides the ability to segregate soybean populations into the correct testing environment, without having to conduct a preliminary progeny test on the line to identify an appropriate environment. It is also desirable to increase genetic diversity by crossing soybeans line with disparate reproductive habits, such as late flowering by early flowering crosses. This process has been utilized with limited success in the past due to the low frequency of desirable segregates that have specific reproductive periods for the target area of adaptation environment. By utilizing molecular markers associated with reproductive growth, a breeder can identify plants in early generations which likely will have reproductive characteristics for the target environment, rather than having to phenotype and select a preferred reproductive growth phenotype in a previous growing season, therefore saving time and other resources. For example, a parent with relative maturity (RM) of 3.1 crossed with a second parent with RM 1.7 will produce progeny with an expected RM range from about 1.5 to about 3.5. If the breeder is only interested in testing the lines from this population that are <2.0 RM, the breeder would have to grow out a large number of progeny and select only those that mature as <2.0 RM. But, using molecular markers associated with reproductive growth, single plants can be selected having a <2.0 RM by selecting preferred locus, allele, haplotype, and/or marker profile. It is also desirable to increase the amount of time a soybean plant is in the reproductive growth stage. For example, one could select for an earlier flowering date without affecting the pod maturity.

Nucleotide polymorphisms, including SNPs as well as insertions/deletions (INDELs) have been identified that are closely linked to and in linkage disequilibrium (LD) with the reproductive growth loci in soybean. These polymorphisms allow for marker-assisted selection (MAS) of these loci, expediting the creation and precise selection soybean plants with a desired reproductive growth phenotype. This will allow for more precision in developing varieties tailored to a particular environment.

At least eight loci affecting flowering and maturity, known as E genes (E1-E8), have been identified (see, e.g., Cober et al. (1996) Crop Sci 36:601-605; Cober et al. (1996) Crop Sci 36:606-610; Asumadu et al. (1998) Ann Bot 82:773-778; Cober et al. (2001) Crop Sci 41:721-727; Abe et al. (2003) Crop Sci 43:1300-1304; Tasma & Shoemaker (2003) Crop Sci 41:319-328; Cober & Voldeng (2001) Crop Sci 41:698-701; Cober & Voldeng (2001) Crop Sci 41:1823-1926; and, Cober et al. (2010) Crop Sci 50:524-527). The E1, E2, and E3 loci have been recently cloned and found to encode a nuclear localized E1 protein (Xia et al. (2012) Proc Natl Acad Sci USA doi/10.1073/pnas.1117982109 E2155-E2164), a GIGANTEA homolog (Watanabe et al. (2011) Genetics 188:395-407), and a phytochrome A homolog respectively (Watanabe et al. (2009) Genetics 182:1251-1262). Recessive loss-of-function mutant alleles at these three loci can independently condition earlier flowering phenotypes.

A method for identifying a soybean plant or germplasm having a preferred reproductive growth phenotype, the method comprising detecting a marker profile associated with the preferred reproductive growth in soybean is provided. In some examples, the marker profile associated with preferred reproductive growth is a marker profile associated with reproductive development, time to initiation of flowering (R1), time from planting to initiation of flowering (R1), time from emergence (VE) to initiation of flowering (R1), early flowering, length of reproductive growth (including but not limited to days from initiation of flowering to full maturity (R8)), time from initiation of flowering (R1) to pod fill, length of flowering, time from initiation of flowering (R1) to beginning maturity (R7), time from initiation of flowering (R1) to full maturity (R8), time to full bloom (R2), time from first trifoliate (V1) to pre-flowering (V6), number of flowers, number of pods, yield, and the like. Examples of a desired or preferred reproductive growth phenotype include, but are not limited to, a maximal reproductive growth length, a reduced time from planting to initiation of flowering (R1), an increased time from initiation of flowering (R1) to full maturity (R8), and increased time to maturity, a decrease in relative maturity, a decrease in maturity group, an increase in relative maturity, an increase in maturity group, and the like. In some examples the time from planting to initiation of flowering (R1) is decreased or increased by at least 1, 2, 3, 4, 5, 6, 7, 8, 9, 10, 11, 12, 13, 14, 15, 16, 17, 18, 19, 20, or more days. In some examples the time from initiation of flowering (R1) to full maturity (R8) is decreased or increased by at least 1, 2, 3, 4, 5, 6, 7, 8, 9, 10, 11, 12, 13, 14, 15, 16, 17, 18, 19, 20, or more days. In some examples yield is increased by at least 1, 2, 3, 4, 5, 6, 7, 8, 9, 10, 11, 12, 13, 14, 15, 16, 17, 18, 19, 20, or more bushels/acre. In some examples yield is increased by at least 1, 2, 3, 4, 5, 6, 7, 8, 9, 10, 11, 12, 13, 14, 15, 16, 17, 18, 19, 20, or more bushels/acre. In some examples yield is increased by at least 1%, 2%, 3%, 4%, 5%, 6%, 7%, 8%, 9%, 10%, 11%, 12%, 13%, 14%, 15%, 16%, 17%, 18%, 19%, 20% or more. A desired or preferred reproductive growth phenotype is typically evaluated by comparison to the reproductive growth phenotype of one or more of a parent line and/or a check variety grown under essentially the same environmental conditions, wherein the parent line or check variety does not have the marker profile associated with preferred reproductive growth phenotype.

In some examples, the method involves detecting marker profile associated with reproductive growth in soybean. In some examples the method comprises detecting a marker profile comprising polymorphisms from two or more linkage group selected from the group consisting of LG C2 (ch 6), LG O (10), and LG L (19), or any combination thereof. In some examples the method comprises detecting at least one locus genetically linked to at least one allele of the marker profile. In some examples the method the at least one locus is within 30 cM of the least one allele of the marker profile. In some examples the method the at least one locus is within about 0-25 cM, 0-20 cM, 0-15 cM, 0-10 cM, 0-5 cM, or about 0-2.5 cM of the at least one allele of the marker profile. In some examples the at least one locus is within about 0-50 kb, 0-100 kb, 0-200 kb, 0-500 kb, 0-750 kb, or about 0-1000 kb of the at least one allele of the marker profile.

In some examples the method comprises detecting at least one allele linked to a marker locus selected from the group consisting of S03703-1, S16601-001, and S01574-1 or any combination thereof. In some examples the method comprises detecting at least one allele within about 0-25 cM, 0-20 cM, 0-15 cM, 0-10 cM, 0-5 cM, or about 0-2.5 cM of a marker locus selected from the group consisting of S03703-1, S16601-001, and S01574-1 or any combination thereof. In some examples the method comprises detecting at least one allele within about 0-50 kb, 0-100 kb, 0-200 kb, 0-500 kb, 0-750 kb, or about 0-1000 kb of a marker locus selected from the group consisting of S03703-1, S16601-001, and S01574-1 or any combination thereof. In some examples, the method comprises detecting at least one allele using at least one marker selected from the group consisting of S03703-1-Q1, S16601-001-Q001, and S01574-1-A, or any combination thereof. In some examples, the method comprises detecting at least one allele selected from the group consisting of a C allele for marker S03703-1-Q1, an T allele for marker S03703-1-Q1, a C allele for marker S16601-001-Q001, an A allele for marker S16601-001-Q001, a C allele for marker S01574-1-A, and an A allele for S01574-1-A, or any combination thereof.

In other examples, the method involves detecting a marker profile comprising two or more marker loci, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 marker loci, or more. In certain examples, the marker profile comprises two or more markers selected from the group consisting of S03703-1-Q1, S16601-001-Q001, and S01574-1-A or any combination thereof. In further examples, the marker profile comprises markers from the set of markers described in Table 10.

In some examples the method uses marker assisted selection to stack two or more loci in a soybean plant, cell, seed, or germplasm. In some examples the method uses a marker profile to produce a soybean plant, cell, seed, or germplasm having a desired predicted flowering time. In some examples the desired predicted flowering time, is a desired flowering time for a specific adapted growing zones or area of adaptability, including but not limited to day length, latitude, environmental class, management zone, maturity group and/or relative maturity. In some examples, the area of adaptability may include using soybean to produce a second crop during a growing season. Second crops are commonly planted in areas with longer growing seasons, however the selected crop may need different reproductive characteristics to be adapted for the second growing cycle in the season than it would for the first growing cycle of the season. Any method of environmental classification can be used, including but not limited to those described in U.S. Pat. No. 8,032,389, and Loeffler et al. (2005) Crop Sci 45:1708-1716, each of which is herein incorporated by reference in its entirety. In certain examples, the marker profile comprises two or more markers selected from the group consisting of S03703-1, S16601-001, and S01574-1 or any combination thereof. In further examples, the marker profile comprises at least one marker from the set of markers described in Table 10.

In further examples, the one or more marker locus detected comprises one or more markers within one or more of the genomic DNA regions of SEQ ID NOs: 1-15. In other examples, the one or more marker locus detected comprises one or more markers within one or more of the genomic regions of SEQ ID NOs: 5, 10, or 15. In some examples, the one or more polymorphism detected may be less than 1 cM, 1 cM, 5 cM, 10 cM, 15 cM, 20 cM, or 30 cM from SEQ ID NOs: 1-15.

In some examples, the method comprises detecting a marker profile comprising at locus genetically linked to at least one allele at a position selected from the group consisting of Gm06:20084642, Gm19:47535046, and Gm10:44725777, or any combination thereof. In some examples, the method comprises detecting a marker profile comprising two or more of the polymorphisms linked to marker loci, said loci comprising a polymorphism selected from the group consisting of Gm06:20084642, Gm19:47535046, and Gm10:44725777, or any combination thereof. In other examples, the marker profile comprises two or more polymorphisms described in Table 10. In some examples, the marker profile may comprise a combination of early alleles and late alleles. In some examples, the at least one favorable or preferred allele of one or more marker loci is selected from the group consisting of an allele of a marker provided in Table 10.

Detecting may comprise isolating nucleic acids, amplifying the marker locus or a portion of the marker locus and detecting the resulting amplified marker amplicon. In particular examples, the amplifying comprises admixing an amplification primer or amplification primer pair and, optionally at least one nucleic acid probe, with a nucleic acid isolated from the first soybean plant or germplasm, wherein the primer or primer pair and optional probe is complementary or partially complementary to at least a portion of the marker locus and is capable of initiating DNA polymerization by a DNA polymerase using the soybean nucleic acid as a template; and, extending the primer or primer pair in a DNA polymerization reaction comprising a DNA polymerase and a template nucleic acid to generate at least one amplicon. In particular examples, the detection comprises real time PCR analysis.

In still further aspects, the information disclosed herein regarding marker alleles, haplotypes, and/or marker profiles can be used to aid in the creation and/or selection of breeding plants, lines, and populations for a preferred reproductive growth phenotype, including but not limited to at least one or more of a preferred time to initiation of flowering, early flowering, relative maturity, and/or length of reproductive growth. Further, the marker alleles, haplotypes, and/or marker profiles can be used for use in introgression into elite soybean germplasm, exotic soybean germplasm, or any other soybean germplasm. In some examples the marker alleles, haplotypes, and/or marker profiles can be used to aid in the creation and/or selection of breeding plants, lines, and populations for a preferred reproductive growth phenotype for a specific area of adaptation or target environment. Also provided is a method for introgressing a soybean QTL, marker, haplotype, and/or marker profile associated with at least a preferred time or length of at least one reproductive stage into soybean germplasm. Methods are provided wherein one or more loci, markers, haplotypes and/or marker profiles are used to create and/or select soybean plants having at a preferred time or length of at least one reproductive stage. Plants so created and selected can be used in a soybean breeding program. Through the process of introgression, the QTL, marker, haplotype, and/or marker profile associated with a preferred time or length of at least one reproductive stage, such as a preferred time to initiation of flowering, early flowering, and/or length of reproductive growth, is introduced from plants identified using marker-assisted selection (MAS) to other plants. According to the method, agronomically desirable plants and seeds can be produced containing the QTL, marker, haplotype, and/or marker profile associated with a preferred time or length of at least one reproductive stage from germplasm containing the QTL, marker, haplotype, and/or marker profile.

Also provided herein is a method for producing a soybean plant adapted for a preferred reproductive growth phenotype. First, donor soybean plants for a parental line containing at least one preferred reproductive growth QTL, marker, haplotype and/or marker profile are selected. According to the method, selection can be accomplished via MAS as explained herein. Selected plant material may represent, among others, an inbred line, a hybrid line, a heterogeneous population of soybean plants, or an individual plant. According to techniques well known in the art of plant breeding, this donor parental line is crossed with a second parental line. In some examples, the second parental line is a high yielding line. This cross produces a segregating plant population composed of genetically heterogeneous plants. Plants of the segregating plant population are screened for the reproductive growth QTL, marker, haplotype, and/or marker profile. Further breeding may include, among other techniques, additional crosses with other lines, hybrids, backcrossing, or self-crossing. The result is a line of soybean plants that has a preferred reproductive growth phenotype and optionally also has other desirable traits from one or more other soybean lines.

Also provided is a method of soybean plant breeding comprising crossing at least two different soybean parent plants, wherein the parent soybean plants differ in time to R1 reproductive stage, obtaining a population of progeny soybean seed from said cross, genotyping the progeny soybean seed with at least one genetic marker, and, selecting a subpopulation comprising at least one soybean seed possessing a genotype for altered time to R1 reproductive stage, wherein the mean time to R1 reproductive stage of the selected subpopulation is altered as compared to the mean time to R1 reproductive stage of the non-selected progeny. In some examples the mean time to R1 reproductive stage of the selected subpopulation of progeny is at least 3-7 days different, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or more days different than the mean time to R1 reproductive stage of the non-selected progeny. In other examples the mean time to R1 reproductive stage of the selected subpopulation of progeny is at least 2, 3, 4, 5, 6, 7, or 8 days different than the mean time to R1 reproductive stage of the non-selected progeny. In some examples, the two different soybean parent plants also differ by maturity. The maturity groups of the parent plants may differ by one or more maturity subgroups, by one or more maturity groups, or by 1 or more days to maturity. In some examples the parents differ in maturity by at least 10 days, between 10 days-20 days, between 10 days-30 days, by at least 0.1, 0.2, 0.3. 0.4, 0.5, 0.6, 0.7, 0.8, or 0.9 maturity subgroups, by at least 1, 2, 3. 4, 5, 6, 7, 8, 9, 10, 11, or 12 maturity groups. In some examples one parent is adapted for a northern growing region, and the second parent is not adapted for a northern growing region. In some examples the parent adapted for a northern growing region comprises a better reproductive growth phenotype for a northern growing region than the parent not adapted for a northern growing region. In some examples, the method further comprises obtaining progeny better adapted for a northern growing region.

In some examples the methods include identifying trait loci in a mixed defined plant population comprising multiple plant families (see, e.g., U.S. Pat. No. 6,399,855, herein incorporated by reference in its entirety). The method comprises quantifying a phenotypic trait across lines sampled from the population, identifying at least one genetic marker associated with the phenotypic trait by screening a set of markers and identifying the quantitative trait loci based on the association of the phenotypic trait and the genetic marker(s). In some examples the plant population consists of diploid plants, either hybrid or inbred. The phenotypic traits associated with the locus are quantitative such that a numerical value can be ascribed to the trait, and the association of the genetic loci and the phenotypic trait is determined through specified statistical models. In some examples the statistical models are linear models with fixed effects and random effects. In other examples the statistical model is a mixed effects model.

Soybean plants, seeds, tissue cultures, variants and mutants having a preferred reproductive growth phenotype produced by the foregoing methods are also provided. Soybean plants, seeds, tissue cultures, variants and mutants comprising one or more of the marker loci, one or more of the favorable alleles, and/or one or more of the haplotypes and having a preferred reproductive growth phenotype are provided. Also provided are isolated nucleic acids, kits, and systems useful for the identification, prediction, and/or selection methods disclosed herein.

In some examples, the soybean plant, germplasm, plant part, or seed having a preferred reproductive growth phenotype further comprises one or more other traits of interest including but not limited to improved resistance to one or more ALS-inhibiting herbicides, a hydroxyphenylpyruvate-dioxygenase inhibitor, a phosphanoglycine (including but not limited to a glyphosate), a sulfonamide, an imidazolinone, a bialaphos, a phosphinothricin, a metribuzin, a mesotrione, an isoxaflutole, an azafenidin, a butafenacil, a sulfosate, a glufosinate, a dicamba, a 2,4-D, and a protox inhibitor. In some examples, resistance to the herbicidal formulation is conferred by a transgene. In some examples, the plant or germplasm further comprises a trait selected from the group consisting of drought tolerance, stress tolerance, disease resistance, herbicide resistance, enhanced yield, modified oil, modified protein, tolerance to chlorotic conditions, and insect resistance, or any combination thereof. In some examples, the trait is selected from the group consisting of brown stem rot resistance, charcoal rot drought complex resistance, *Fusarium* resistance, *Phytophthora* resistance, stem canker resistance, sudden death syndrome resistance, *Sclerotinia* resistance, *Cercospora* resistance, anthracnose resistance, target spot resistance, frogeye leaf spot resistance, soybean cyst nematode resistance, root knot nematode resistance, rust resistance, high oleic content, low linolenic content, aphid resistance, stink bug resistance, and iron chlorosis deficiency tolerance, or any combination thereof. In some examples, one or more of the traits is conferred by one or more transgenes, by one or more native loci, or any combination thereof.

In another example a method of producing a cleaned soybean seed is provided, the method comprising cleaning a soybean seed having at least one locus conferred a preferred reproductive growth phenotype is provided. In some examples, the cleaned soybean seed has enhanced yield characteristics when compared to a soybean seed which has not been cleaned. Cleaned soybean seed produced by the methods are also provided.

In another example a method of producing a treated soybean seed is provided, the method comprising treating a soybean seed having at least one locus conferred a preferred reproductive growth phenotype is provided. In some examples, the seed treatment comprises a fungicide, an insecticide, or any combination thereof. In some examples the seed treatment comprises trifloxystrobin, metalaxyl, imidacloprid, *Bacillus* spp., and any combination thereof. In some examples the seed treatment comprises picoxystrobin, penthiopyrad, cyantraniliprole, chlorantraniliprole, and any combination thereof. In some examples, the seed treatment improves seed germination under normal and/or stress environments, early stand count, vigor, yield, root formation, nodulation, and any combination thereof when compared to a soybean seed which has not been treated. In some examples seed treatment reduces seed dust levels, insect damage, pathogen establishment and/or damage, plant virus infection and/or damage, and any combination thereof. Treated soybean seed produced by the methods are also provided.

It is to be understood that this invention is not limited to particular embodiments, which can, of course, vary. It is also to be understood that the terminology used herein is for the purpose of describing particular embodiments only, and is not intended to be limiting. Further, all publications referred to herein are incorporated by reference for the purpose cited to the same extent as if each was specifically and individually indicated to be incorporated by reference herein.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of" Similarly, the term "consisting essentially of" is intended to include examples encompassed by the term "consisting of."

Certain definitions used in the specification and claims are provided below. In order to provide a clear and consistent understanding of the specification and claims, including the scope to be given such terms, the following definitions are provided:

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic association or linkage relationships among loci on one or more chromosomes (or linkage groups) within a given species, generally depicted in a diagrammatic or tabular form.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, marker, haplotype, marker profile, trait, or trait locus from the genome of one plant into the genome of another plant.

The terms "label" and "detectable label" refer to a molecule capable of detection. A detectable label can also include a combination of a reporter and a quencher, such as are employed in FRET probes or TAQMAN® probes. The term "reporter" refers to a substance or a portion thereof that is capable of exhibiting a detectable signal, which signal can be suppressed by a quencher. The detectable signal of the reporter is, e.g., fluorescence in the detectable range. The term "quencher" refers to a substance or portion thereof that is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between two genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, disease tolerance, stress tolerance, reproductive growth, etc.).

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers, the lower the frequency of recombination, the greater the degree of linkage.

"Linkage disequilibrium" is a non-random association of 2 or more alleles wherein the 2 or more alleles occur together at a greater frequency than expected from their individual frequencies.

"Linkage group" refers to traits or markers that cosegregate. A linkage group generally corresponds to a chromosomal region containing genetic material that encodes the traits or markers.

"Locus" is a defined segment of DNA.

A "management zone" is any specific area within a field that responds to management practices in a similar way. There are various criteria and ways to create management zones, including but not limited to using soil data, climate information, geographic data, and/or crop information in conjunction with an algorithm to identify areas of a field that are most similar. The computer can take thousands of numbers and find areas that are alike, cluster them together, and generate a map. Different zones can be defined by using different data inputs, but weighting inputs differently, by assigning different criteria, or by identifying different management practices of interest. For example a management zone for irrigation is probably not identical to a management zone for weed management for the same field in the same year. Management zones may also use the same inputs and criteria and yet differ across years.

A "map location," a "map position," or a "relative map position" is an assigned location on a genetic map relative to linked genetic markers where a specified marker can be found within a given species. Map positions are generally provided in centimorgans (cM), unless otherwise indicated, genetic positions provided are based on the Glycine max consensus map v 4.0 as provided by Hyten et al. (2010) Crop Sci 50:960-968. A "physical position" or "physical location" is the position, typically in nucleotide bases, of a particular nucleotide, such as a SNP nucleotide, on the chromosome. Unless otherwise indicated, the physical position within the soybean genome provided is based on the Glyma 1.0 genome sequence described in Schmutz et al. (2010) Nature 463:178-183, available from the Phytozome website (phytozome-dot-net/soybean).

"Mapping" is the process of defining the association and relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Any detectable polymorphic trait can be used as a marker so long as it is inherited differentially and exhibits non-random association with a phenotypic trait of interest.

"Marker assisted selection" refers to the process of selecting a desired trait or traits in a plant or plants by detecting one or more nucleic acids from the plant, where the nucleic acid is associated with or linked to the desired trait, and then selecting the plant or germplasm possessing those one or more nucleic acids.

"Maturity Group" is an agreed-on industry division of groups of varieties, based on the zones in which they are adapted primarily according to day length and/or latitude. Soybean varieties are grouped into 13 maturity groups, depending on the climate and latitude for which they are adapted. Soybean maturities are divided into relative maturity groups (denoted as 000, 00, 0, I, II, III, IV, V, VI, VII, VIII, IX, X, or 000, 00, 0, 1, 2, 3, 4, 5, 6, 7, 8, 9, 10). These maturity groups are given numbers, with numbers 000, 00, 0 and 1 typically being adapted to Canada and the northern United States, groups VII, VIII and IX being grown in the southern regions, and Group X is tropical. Within a maturity group are sub-groups. A subgroup is a tenth of a relative maturity group (for example 1.3 would indicate a group 1 and subgroup 3). Within narrow comparisons, the difference of a tenth of a relative maturity group equates very roughly to a day difference in maturity at harvest.

A "mixed defined plant population" refers to a plant population containing many different families and lines of plants. Typically, the defined plant population exhibits a quantitative variability for a phenotype that is of interest. "Multiple plant families" refers to different families of related plants within a population.

"Haplotype" refers to a combination of particular alleles present within a particular plant's genome at two or more linked marker loci, for instance at two or more loci on a particular linkage group. For instance, in one example, two specific marker loci on LG A1 are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

As used herein, a "marker profile" means a combination of particular alleles present within a particular plant's genome at two or more marker loci which are not linked, for instance two or more loci on two or more different linkage groups or two or more chromosomes. For instance, in one example, one marker locus on LG A1 and a marker locus on another linkage group are used to define a marker profile for a particular plant. In certain other examples a plant's marker profile comprises one or more haplotypes. In some examples, the marker profile encompasses two or more loci for the same trait, such as time to first flower. In other examples, the marker profile encompasses two or more loci associated with two or more traits of interest, such as time to first flower and a second trait of interest.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells, and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Reproductive stage" is a description of the characteristics associated with various phases of reproductive growth.

"R1" is the first reproductive stage when soybean begins to bloom by producing the first flower.

"Time to R1 reproductive stage" is measured in days unless otherwise stated.

"Tolerance and "improved tolerance" are used interchangeably herein and refer to any type of increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

"Self-crossing" or "self-pollination" or "selfing" is a process through which a breeder crosses a plant with itself; for example, a second-generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors.

An "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media, or other chemical components.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Sambrook").

Soybean is a short-day crop and its development is largely determined by variety-specific day length requirements that initiate floral development. In other words, as the days grow shorter soybean will flower and enter into reproductive development stages. Due to this photoperiod requirement, days from planting until maturity cannot be accurately estimated for soybean due to variation in planting date and other environmental variations. After flowering, temperature drives development and the days until maturity can be estimated. The number of days from floral initiation (R1) until physiological maturity (R7) is usually independent of variety, but will vary slightly from year to year due to temperature differences between years. Although most sensitive to day length, soybean flowering will be delayed to some extent with later planting dates. However, later planted soybean initiates flowering during a warmer time of the year; therefore, post-flower development speeds up. The precise number of days from full flower (R2) until R7 cannot be predicted, but fairly reliable estimates can be derived from historical information (see, e.g., Holshouser (2010) "Days to Soybean Physiological Maturity," Virginia Cooperative Extension, Bulletin 3009-1459; and, Heatherly (2005) "Soybean maturity group, planting date and development related," Delta Farm Press, Oct. 14, 2005).

Soybean growth is often characterized as comprising two stages: vegetative growth and reproductive growth. The vegetative (V) stages are numbered according to how many fully-developed trifoliate leaves are present. The reproductive (R) stages begin at flowering and include pod development, seed development, and plant maturation. Soybean yield is impacted by genetics and environment, and various management practices can impact crop growth and yield in the context of the genetics of the crop. These stages are well-characterized and known (see, e.g., McWilliams et al. (1999) Soybean Growth & Management Quick Guide, A-1174, NDSU Extension Service), and summarized in the table below.

| Vegetative Stages | | Reproductive Stages |
|---|---|---|
| VE | Emergence | R1 beginning bloom, 1$^{st}$ flower |
| VC | Cotyledon Stage | R2 full bloom, flower in top 2 nodes |
| V1 | 1st trifoliate leaf | R3 beginning pod, $\frac{3}{16}$" pod in top 4 nodes |
| V2 | 2$^{nd}$ trifoliate | R4 full pod, $\frac{3}{4}$" pod in top 4 nodes |
| V3 | 3$^{rd}$ trifoliate | R5 $\frac{1}{8}$" seed in top 4 nodes |
| Vn | nth trifoliate | R6 full size seed in top 4 nodes |
| V6 | flowering should start soon | R7 beginning maturity, one mature pod |
| | | R8 full maturity, 95% of pods are mature |

The advent of molecular genetic markers has facilitated mapping and selection of agriculturally important traits in soybean. Markers tightly linked to trait genes are an asset in the rapid identification of soybean lines carrying the trait gene on the basis of genotype by the use of marker assisted selection (MAS). Introgressing trait genes into a desired cultivar would also be facilitated by using suitable markers.

Soybean cultivar development for preferred reproductive growth phenotype can be performed using classical breeding methods or by using marker assisted selection (MAS). Genetic markers for maturity or flowering time have been identified.

Provided are markers, haplotypes, and/or marker profiles associated with a preferred reproductive growth phenotype, as well as related primers and/or probes and methods for the use of any of the foregoing for identifying and/or selecting soybean plants with preferred time to floral initiation. A method for determining the presence or absence of at least one allele of a particular marker, haplotype, and/or marker profile associated with floral initiation comprises analyzing genomic DNA from a soybean plant or germplasm to determine if at least one, or a plurality, of such markers is present or absent and if present, determining the allelic form of the marker(s). If a plurality of markers on a single linkage group is investigated, this information regarding the markers present in the particular plant or germplasm can be used to determine a haplotype for that plant/germplasm.

In certain examples, plants or germplasm are identified that have at least one favorable allele, marker, haplotype and/or marker profile that positively correlate a preferred reproductive growth phenotype. However, in other examples, it is useful to identify alleles, markers, haplotypes and/or marker profiles that negatively correlate with a preferred reproductive growth phenotype, for example to eliminate such plants or germplasm from subsequent rounds of breeding, or to use as controls or check. Soybean plants, cells, seed, varieties, and/or germplasm having preferred reproductive growth phenotype are provided.

Any marker associated with a preferred reproductive growth phenotype locus or QTL is useful. Further, any suitable type of marker can be used, including Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers known in the art or phenotypic traits may also be used as markers in the methods.

Markers that map closer to a QTL are generally used over markers that map farther from such a QTL. Marker loci are especially useful when they are closely linked to a locus associated with a preferred reproductive growth phenotype. Thus, in one example, marker loci display an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less with a QTL to which they are linked. Thus, the loci are separated from the QTL to which they are linked by about 10 cM, 9 cM, 8 cM, 7 cM, 6 cM, 5 cM, 4 cM, 3 cM, 2 cM, 1 cM, 0.75 cM, 0.5 cM, or 0.25 cM or less. In certain examples, multiple marker loci that collectively make up a haplotype and/or a marker profile are investigated, comprising for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci.

In addition to the markers discussed herein, information regarding useful soybean markers can be found, for example, on the USDA's Soybase website, available at www.soybase.org. A number of soybean markers have been mapped and linkage groups created, as described in Cregan et al. (1999) Crop Sci 39:1464-90, Choi et al. (2007) Genetics 176:685-96, and Hyten, et al. (2010) Crop Sci 50:960-968, each of which is herein incorporated by reference in its entirety, including any supplemental materials associated with the publication. Many soybean markers are publicly available at the USDA affiliated soybase website (at soybase-dot-org). One of skill in the art will recognize that the identification of favorable marker alleles may be germplasm-specific. In addition to the markers listed in the Table 10, other closely linked markers could also be useful for detecting and/or selecting soybean plants with a preferred reproductive growth phenotype. For other marker loci useful to identify a preferred reproductive growth genotype and phenotype, see, for example PCT/US2014/21517 "Compositions Associated with Soybean Reproductive Growth and Methods of Use" which discloses many loci, markers, alleles, polymorphisms, chromosomal intervals, haplotypes, and/or marker profiles which can be used alone or in combination with the markers provided herein, the disclosure of PCT/US2014/21517 is herein incorporated by reference. One of skill will also recognize that methods for identifying the favorable alleles are routine and well known in the art, and furthermore, that the identification and use of such favorable alleles is well within the scope of the invention.

The use of marker assisted selection (MAS) to select a soybean plant or germplasm based upon detection of a particular polymorphism, locus, marker, haplotype, and/or marker profile of interest is provided. For instance, in certain examples, a soybean plant or germplasm possessing a certain predetermined favorable marker allele, haplotype, and/or marker profile will be selected via MAS. Using MAS, soybean plants or germplasm can be selected for markers or marker alleles that positively correlate with a desired trait, without actually raising soybean and measuring for the desired trait (or, contrawise, soybean plants can be selected against if they possess markers that negatively correlate with the desired trait). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some examples, molecular markers are detected using a suitable amplification-based detection method. Typical amplification methods include various polymerase based replication methods, including the polymerase chain reaction (PCR), ligase mediated methods, such as the ligase chain reaction (LCR), and RNA polymerase based amplification (e.g., by transcription) methods. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage & Caruthers (1981) Tetrahedron Letts 22:1859-1862, e.g., using a commercially available automated synthesizer, e.g., as described in Needham-VanDevanter et al. (1984) Nucl Acids Res 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair, or probe. For example, primers can be designed using any suitable software program, such as LASERGENE® or Primer3.

The primers are not limited to generating an amplicon of any particular size. For example, the primers used to amplify the marker loci and alleles herein are not limited to amplifying the entire region of the relevant locus. In some examples, marker amplification produces an amplicon at least 20 nucleotides in length, or alternatively, at least 50 nucleotides in length, or alternatively, at least 100 nucleotides in length, or alternatively, at least 200 nucleotides in length, or alternatively, at least 300 nucleotides in length, or alternatively, at least 400 nucleotides in length, or alternatively, at least 500 nucleotides in length, or alternatively, at least 1000 nucleotides in length, or alternatively, at least 2000 nucleotides in length or more.

PCR, RT-PCR, and LCR are common amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous references, such as Mullis et al. (1987) U.S. Pat. No. 4,683,202; Arnheim & Levinson (1990) C&EN 36-47; Kwoh et al. (1989) Proc Natl Acad Sci USA 86:1173; Guatelli et al. (1990) Proc Natl Acad Sci USA 87:1874; Lomell et al. (1989) J Clin Chem 35:1826; Landegren et al. (1988) Science 241:1077-1080; Van Brunt (1990) Biotechnology 8:291-294; Wu & Wallace (1989) Gene 4:560; Barringer et al. (1990) Gene 89:117; and Sooknanan & Malek (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype alleles, such as SNP alleles, are provided. For example, exemplary primers and probes are provided herein. However, one of skill will immediately recognize that other primer and probe sequences could also be used. For instance, primers to either side of the given primers can be used in place of the given primers, so long as the primers can amplify a region that includes the allele to be detected, as can primers and probes directed to other marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and their corresponding detection strategies can be found, e.g., in Haugland (1996) *Handbook of Fluorescent Probes and Research Chemicals Sixth Edition* by Molecular Probes, Inc. (Eugene, Oreg.); or Haugland (2001) *Handbook of Fluorescent Probes and Research Chemicals Eighth Edition* by Molecular Probes, Inc. (Eugene, Oreg.).

Detectable labels may also include reporter-quencher pairs, such as are employed in Molecular Beacon and TAQMAN® probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent. Generally, whether the quencher is fluorescent or simply releases the transferred energy from the reporter by nonradiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules*, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland (2001) *Handbook of Fluorescent Probes and Research Chemicals Eighth Edition* by Molecular Probes, Inc. (Eugene, Oreg.), the content of which is incorporated herein by reference.

In certain examples, reporter-quencher pairs are selected from xanthene dyes including fluorescein and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters is the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TAQMAN® probes. A molecular beacon (MB) is an oligonucleotide that, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone et al. (1995) Nucl Acids Res 26:2150-2155; Tyagi & Kramer (1996) Nat Biotechnol 14:303-308; Blok & Kramer (1997) Mol Cell Probes 11:187-194; Hsuih et al. (1997) J Clin Microbiol 34:501-507; Kostrikis et al. (1998) Science 279: 1228-1229; Sokol et al. (1998) Proc Natl Acad Sci USA 95:11538-11543; Tyagi et al. (1998) Nat Biotechnol 16:49-53; Bonnet et al. (1999) Proc Natl Acad Sci USA 96:6171-6176; Fang et al. (1999) J Am Chem Soc 121:2921-2922; Marras et al. (1999) Genet Anal Biomol Eng 14:151-156; and, Vet et al. (1999) Proc Natl Acad Sci USA 96:6394-6399. Additional details regarding MB construction and use are also found in the patent literature, e.g., U.S. Pat. Nos. 5,925,517; 6,150,097; and 6,037,130.

Another real-time detection method is the 5'-exonuclease detection method, also called the TAQMAN® assay, as set forth in U.S. Pat. Nos. 5,804,375; 5,538,848; 5,487,972; and 5,210,015, each of which is hereby incorporated by reference in its entirety. In the TAQMAN® assay, a modified probe, typically 10-30 nucleotides in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are typically attached to the probe within a few nucleotides of one another, usually within 30 nucleotides of one another, or within 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

One example of a suitable real-time detection technique that does not use a separate probe that binds intermediate to the two primers is the KASPar detection system/method, which is well known in the art. In KASPar, two allele specific primers are designed such that the 3' nucleotide of each primer hybridizes to the polymorphic base. For example, if the SNP is an A/C polymorphism, one of the primers would have an "A" in the 3' position, while the other primer would have a "C" in the 3' position. Each of these two allele specific primers also has a unique tail sequence on the 5' end of the primer. A common reverse primer is employed that amplifies in conjunction with either of the two allele specific primers. Two 5' fluor-labeled reporter oligos are also included in the reaction mix, one designed to interact with each of the unique tail sequences of the allele-specific primers. Lastly, one quencher oligo is included for each of the two reporter oligos, the quencher oligo being complementary to the reporter oligo and being able to quench the fluor signal when bound to the reporter oligo. During PCR, the allele-specific primers and reverse primers bind to complementary DNA, allowing amplification of the amplicon to take place. During a subsequent cycle, a complementary nucleic acid strand containing a sequence complementary to the unique tail sequence of the allele-specific primer is created. In a further cycle, the reporter oligo interacts with this complementary tail sequence, acting as a labeled primer. Thus, the product created from this cycle of PCR is a fluorescently-labeled nucleic acid strand. Because the label incorporated into this amplification product is specific to the allele specific primer that resulted in the amplification, detecting the specific fluor presenting a signal can be used to determine the SNP allele that was present in the sample.

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook et al. *Molecular Cloning—A Laboratory Manual* (3d ed.) Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel"); and, *PCR Protocols A Guide to Methods and Applications* (Innis et al., eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH) or nucleic acid sequencing techniques. ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Isolated polynucleotide or fragments thereof are capable of specifically hybridizing to other nucleic acid molecules under appropriate conditions. In one example, the nucleic acid molecules comprise any of SEQ ID NOs: 1-15, complements thereof and fragments thereof. In another aspect, the nucleic acid molecules of the present invention include nucleic acid molecules that hybridize, for example, under high or low stringency, substantially homologous sequences, or that have both to these molecules. Conventional stringency conditions are described by Sambrook et al. In: Molecular Cloning, A Laboratory Manual, 2nd Edition, Cold Spring Harbor Press, Cold Spring Harbor, N.Y. (1989)), and by Haymes et al. In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In some examples, an a marker locus will specifically hybridize to one or more of the nucleic acid molecules set forth in SEQ ID NOs: 1-15 or complements thereof or fragments of either under moderately stringent conditions, for example at about 2.0×SSC and about 65° C. In an aspect, a nucleic acid of the present invention will specifically hybridize to one or more SEQ ID NOs: 1-15 or complements or fragments of either under high stringency conditions.

In some examples, a marker associated with a preferred reproductive growth phenotype comprises any one of SEQ ID NOs: 1-15 or complements or fragments thereof. In other examples, a marker has between 80%, 85%, 90%, 91%, 92%, 93%, 94%, 95%, 96%, 97%, 98%, 99%, or 100% sequence identity to any one of SEQ ID NOs: 1-15 or complements or fragments thereof. Unless otherwise stated, percent sequence identity is determined using the GAP program is default parameters for nucleic acid alignment (Accelrys, San Diego, Calif., USA).

Traits or markers are considered herein to be linked if they generally co-segregate. A 1/100 probability of recombination per generation is defined as a map distance of 1.0 centiMorgan (1.0 cM). The genetic elements or genes located on a single chromosome segment are physically linked. In some embodiments, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 9, 8, 7, 6, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 9%, 8%, 7%, 6%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

Markers are used to define a specific locus on the soybean genome. Each marker is therefore an indicator of a specific segment of DNA, having a unique nucleotide sequence. Map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans.

Favorable genotypes associated with at least trait of interest may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to nextgeneration sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis.

In some examples, markers within 1 cM, 5 cM, 10 cM, 15 cM, or 30 cM of SEQ ID NO: 1-15 are provided. Similarly, one or more markers mapped within 1, 5, 10, 20 and 30 cM or less from the markers provided can be used for the selection or introgression of the region associated with a preferred reproductive growth phenotype. In other examples, any marker that is linked with SEQ ID NOs: 1-15 and associated with a preferred reproductive growth phenotype is provided. In other examples, markers provided include a substantially a nucleic acid molecule within 5 kb, 10 kb, 20 kb, 30 kb, 100 kb, 500 kb, 1,000 kb, 10,000 kb, 25,000 kb, 50,000 kb, 0.1 megabases (Mb), 0.2 Mb, 0.3 Mb, 0.4 Mb, 0.5 Mb, 0.6 Mb, 0.7 Mb, 0.8 Mb, 0.9 Mb, or 1 Mb of a marker selected from the group consisting of SEQ ID NOs: 1-15.

Real-time amplification assays, including MB or TAQMAN® based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 13-18 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

To effectuate SNP allele detection, a real-time PCR reaction can be performed using primers that amplify the region including the SNP locus, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

Introgression of a preferred reproductive growth phenotype into a soybean germplasm having an undesired or less preferred reproductive growth phenotype is provided. Any method for introgressing a QTL or marker into soybean plants known to one of skill in the art can be used. Typically, a first soybean germplasm that contains a preferred reproductive growth phenotype derived from a particular polymorphism, locus, marker, haplotype and/or marker profile and a second soybean germplasm that lacks such a reproductive growth phenotype derived from the polymorphism, locus, marker, haplotype and/or marker profile are provided. The first soybean germplasm may be crossed with the second soybean germplasm to provide progeny soybean germplasm. These progeny germplasm are genotyped to determine the presence of a preferred reproductive growth phenotype derived from the polymorphism, locus, marker, haplotype and/or marker profile, and progeny that tests positive for the presence of the polymorphism, locus, marker, haplotype and/or marker profile are selected as being soybean germplasm into which the polymorphism, locus, marker, haplotype and/or marker profile has been introgressed. Methods for performing such screening are well known in the art and any suitable method can be used.

One application of MAS is to use the trait polymorphisms, loci, markers, haplotypes, and/or marker profile to increase the efficiency of an introgression or backcrossing effort aimed at introducing a trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible.

Thus, the markers and methods can be utilized to guide marker assisted selection or breeding of soybean varieties with the desired complement (set) of allelic forms of chromosome segments associated with superior agronomic performance (desired trait, tolerance, along with any other available markers for yield, disease or stress tolerance, etc.). Any of the disclosed marker alleles, haplotypes, and/or marker profiles can be introduced into a soybean line via introgression, by traditional breeding (or introduced via transformation, or both) to yield a soybean plant with superior agronomic performance. The number of alleles associated with a desired trait that can be introduced or be present in a soybean plant ranges from 1 to the number of alleles disclosed herein, each integer of which is incorporated herein as if explicitly recited.

This also provides a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with a desired trait and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant that comprises at least one of the markers, haplotypes, and/or marker profile associated with the desired trait, such that the progeny are capable of inheriting the marker, haplotype, and/or marker profile.

Often, a method is applied to at least one related soybean plant such as from progenitor or descendant lines in the subject soybean plants pedigree such that inheritance of the desired trait can be traced. The number of generations separating the soybean plants being subject to the methods will generally be from 1 to 20, commonly 1 to 5, and typically 1, 2, or 3 generations of separation, and quite often a direct descendant or parent of the soybean plant will be subject to the method (i.e., 1 generation of separation).

Genetic diversity is important for long-term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers, haplotypes, marker profiles, primers, and probes can be used for MAS involving crosses of elite lines to exotic soybean lines (elite×exotic) by subjecting the segregating progeny to MAS to maintain major yield alleles, along with the reproductive growth marker alleles herein.

As an alternative to standard breeding methods of introducing traits of interest into soybean (e.g., introgression), transgenic approaches can also be used to create transgenic plants with the desired traits. In these methods, exogenous nucleic acids that encode a desired QTL, marker, haplotype, and/or marker profile are introduced into target plants or germplasm. For example, a nucleic acid that codes for a preferred reproductive growth trait is cloned, e.g., via positional cloning, and introduced into a target plant or germplasm.

Experienced plant breeders can recognize the time to R1 reproductive stage trait for soybean plants in the field, and can select the individuals or populations for breeding purposes or for propagation with the desired phenotype. In this context, the plant breeder recognizes "preferred" soybean plants. However, time to R1 is a phenotypic spectrum consisting of extremes in timing, as well as a continuum of intermediate phenotypes. Evaluation of these intermediate phenotypes using reproducible assays are of value to scientists who seek to identify genetic loci that impart a specific time to R1 stage, to conduct marker assisted selection for populations, and to use introgression techniques to breed a specific R1 trait into an elite soybean line, for example.

In some examples, a kit for detecting markers or haplotypes, and/or for correlating the markers or haplotypes with a desired phenotype (e.g., a preferred reproductive growth phenotype), are provided. Thus, a typical kit can include a set of marker probes and/or primers configured to detect at least one favorable allele of one or more marker locus associated with a preferred reproductive growth phenotype. These probes or primers can be configured, for example, to detect the marker alleles noted in the tables and examples herein, e.g., using any available allele detection format, such as solid or liquid phase array based detection, microfluidic-based sample detection, etc. The kits can further include packaging materials for packaging the probes, primers, or instructions; controls, such as control amplification reactions that include probes, primers, and/or template nucleic acids for amplifications; molecular size markers; or the like.

System or kit instructions that describe how to use the system or kit and/or that correlate the presence or absence of the allele with the predicted preferred or non-preferred phenotype are also provided. For example, the instructions can include at least one look-up table that includes a correlation between the presence or absence of the favorable allele(s) and the predicted time to floral initiation. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector.

Isolated nucleic acids comprising a nucleic acid sequence coding for a preferred reproductive growth phenotype, or capable of detecting such a phenotypic trait, or sequences complementary thereto, are also included. In certain examples, the isolated nucleic acids are capable of hybridizing under stringent conditions to nucleic acids of a soybean cultivar phenotyped for a preferred reproductive growth phenotype, to detect loci associated with a preferred reproductive growth phenotype, including one or more of S03703-1, S16601-001, S01574-1, Gm06:20084642, Gm19:47535046, or Gm10:44725777, and any combination thereof.

In some examples the isolated nucleic acids are markers, for example markers selected from the group consisting of S03703-1-Q1, S16601-001-Q001, and S01574-1-A. In some examples the nucleic acid is one of more polynucleotides selected from the group consisting of SEQ ID NOs: 1-15. Vectors comprising one or more of such nucleic acids, expression products of such vectors expressed in a host compatible therewith, antibodies to the expression product (both polyclonal and monoclonal), and antisense nucleic acids are also included. In some examples, one or more of these nucleic acids is provided in a kit.

As the parental line having a preferred reproductive growth phenotype, any line known to the art or disclosed herein may be used. Also included are soybean plants produced by any of the foregoing methods. Seed of a soybean germplasm produced by crossing a soybean variety having an allele, marker, haplotype and/or marker profile associated with time to R1 reproductive stage with a soybean variety lacking such allele, marker, haplotype, and/or marker profile, and progeny thereof, is also included. Soybeans plants and seeds produced by the methods, and/or comprising the marker profile for the preferred reproductive growth phenotype are included and provided herein.

A soybean plant, germplasm, plant part, or seed further comprising resistance to at least one herbicidal formulation is provided. For example, the herbicidal formulation can comprise a compound selected from the group consisting of an ALS-inhibiting herbicide, a glyphosate, a hydroxyphenylpyruvatedioxygenase (HPPD) inhibitor, a sulfonamide, an imidazolinone, a bialaphos, a phosphinothricin, a metribuzin, a mesotrione, an isoxaflutole, an azafenidin, a butafenacil, a sulfosate, a glufosinate, a dicamba, a 2,4-D, and a protox inhibitor. In some examples, resistance to the herbicidal formulation is conferred by a transgene.

Glyphosate resistance can be conferred from genes including but not limited to EPSPS, GAT, GOX, and the like, such as described in U.S. Pat. Nos. 6,248,876; 5,627,061; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE36,449; RE37,287 E; 5,491,288; 5,776,760; 5,463,175; 8,044,261; 7,527,955; 7,666,643; 7,998,703; 7,951,995; 7,968,770; 8,088,972, 7,863,503; and US20030083480; WO 97/04103; WO 00/66746; WO 01/66704; and WO 00/66747, which are each incorporated herein by reference in their entireties for all purposes. Additionally, glyphosate tolerant plants can be generated through the selection of naturally occurring mutations that impart tolerance to glyphosate.

HPPD resistance can be conferred by genes including exemplary sequences disclosed in U.S. Pat. Nos. 6,245,968; 6,268,549; and 6,069,115; and WO 99/23886, which are each incorporated herein by reference in their entireties for all purposes. Mutant hydroxyphenylpyruvatedioxygenases having this activity are also known. For further examples see US20110185444 and US20110185445.

Resistance to auxins, such as 2,4-D or dicamba, can be provided by polynucleotides as described, for example, in WO2005/107437, US20070220629, and U.S. Pat. No. 7,838,733 and in Herman et al. (2005) J. Biol. Chem. 280:24759-24767, each which is herein incorporated by reference.

Resistance to PPO-inhibiting herbicides can be provided as described in U.S. Pat. Nos. 6,288,306; 6,282,837; and 5,767,373; and WO 01/12825, each of which is herein incorporated by reference. Plants containing such polynucleotides can exhibit improved tolerance to any of a variety of herbicides which target the protox enzyme. Resistance can also be conferred as described in US20100186131; US20110185444; US20100024080, each of which is herein incorporated by reference.

The development of plants containing an exogenous phosphinothricin acetyltransferase which confers resistance to glufosinate, bialaphos, or phosphinothricin is described, for example, in U.S. Pat. Nos. 5,969,213; 5,489,520; 5,550,318; 5,874,265; 5,919,675; 5,561,236; 5,648,477; 5,646,024; 6,177,616; and 5,879,903, which are each incorporated herein by reference in their entireties for all purposes. Mutant phosphinothricin acetyltransferase having this activity are also known in the art.

In some examples, the plant or germplasm further comprises a trait selected from the group consisting of drought tolerance, stress tolerance, disease resistance, herbicide resistance, enhanced yield, modified oil, modified protein, tolerance to chlorotic conditions, and insect resistance, or any combination thereof. In some examples, the trait is selected from the group consisting of brown stem rot resistance, charcoal rot drought complex resistance, *Fusarium* resistance, *Phytophthora* resistance, stem canker resistance, sudden death syndrome resistance, *Sclerotinia* resistance, *Cercospora* resistance, anthracnose resistance, target spot resistance, frogeye leaf spot resistance, soybean cyst nematode resistance, root knot nematode resistance, rust resistance, high oleic content, low linolenic content, aphid resistance, stink bug resistance, and iron chlorosis deficiency tolerance, or any combination thereof. In some examples, one or more of the traits is conferred by one or more transgenes, by one or more native loci, or any combination thereof. Examples of markers and loci conferring improved iron chlorosis deficiency tolerance are disclosed in US20110258743, U.S. Pat. No. 7,582,806, and U.S. Pat. No. 7,977,533, each of which is herein incorporated by reference. Various disease resistance loci and markers are disclosed, for example, in WO1999031964, U.S. Pat. No. 5,948,953, U.S. Pat. No. 5,689,035, US20090170112, US20090172829, US20090172830, US20110271409, US20110145953, U.S. Pat. No. 7,642,403, U.S. Pat. No. 7,919,675, US20110131677, U.S. Pat. No. 7,767,882, U.S. Pat. No. 7,910,799, US20080263720, U.S. Pat. No. 7,507,874, US20040034890, US20110055960, US20110185448, US20110191893, US20120017339, U.S. Pat. No. 7,250,552, U.S. Pat. No. 7,595,432, U.S. Pat. No. 7,790,949, U.S. Pat. No. 7,956,239, U.S. Pat. No. 7,968,763, each of which is herein incorporated by reference. Markers and loci conferring improved yield are provided, for example, in U.S. Pat. No. 7,973,212 and WO2000018963, each of which is herein incorporated by reference. Markers and loci conferring improved resistance to insects are disclosed in, for example, US20090049565, U.S. Pat. No. 7,781,648, US20100263085, U.S. Pat. No. 7,928,286, U.S. Pat. No. 7,994,389, and WO2011116131, each of which is herein incorporated by reference. Markers and loci for modified soybean oil content or composition are disclosed in, for example, US20120028255 and US20110277173, each of which is herein incorporated by reference. Methods and compositions to modified soybean oil content are described in, for example, WO2008147935, U.S. Pat. No. 8,119,860; U.S. Pat. No. 8,119,784; U.S. Pat. No. 8,101,189; U.S. Pat. No. 8,058,517; U.S. Pat. No. 8,049,062; U.S. Pat. No. 8,124,845, U.S. Pat. No. 7,790,959, U.S. Pat. No. 7,531,718, U.S. Pat. No. 7,504,563, and U.S. Pat. No. 6,949,698, each of which is herein incorporated by reference. Markers and loci conferring tolerance to nematodes are disclosed in, for example, US20090064354, US20090100537, US20110083234, US20060225150, US20110083224, U.S. Pat. No. 5,491,081, U.S. Pat. No. 6,162,967, U.S. Pat. No. 6,538,175, U.S. Pat. No. 7,872,171, U.S. Pat. No. 6,096,944, and U.S. Pat. No. 6,300,541, each of which is herein incorporated by reference. Resistance to nematodes may be conferred using a transgenic approach as described, for example, in U.S. Pat. No. 6,284,948 and U.S. Pat. No. 6,228,992, each of which is herein incorporated by reference. Plant phenotypes can be modified using isopentyl transferase polynucleotides as described, for example, in U.S. Pat. No. 7,553,951 and U.S. Pat. No. 7,893,236, each of which is herein incorporated by reference.

Soybean seeds, plants, and plant parts comprising a preferred reproductive growth phenotype may be cleaned and/or treated. The resulting seeds, plants, or plant parts produced by the cleaning and/or treating process(es) may exhibit enhanced yield characteristics. Enhanced yield characteristics can include one or more of the following: increased germination efficiency under normal and/or stress conditions, improved plant physiology, growth and/or development, such as water use efficiency, water retention efficiency, improved nitrogen use, enhanced carbon assimilation, improved photosynthesis, and accelerated maturation, and improved disease and/or pathogen tolerance. Yield characteristics can furthermore include enhanced plant architecture (under stress and non-stress conditions), including but not limited to early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield characteristics include seed composition, such as carbohydrate content, protein content, oil content and composition, nutritional value, reduction in anti-nutritional compounds, improved processability and better storage stability.

Cleaning a seed or seed cleaning refers to the removal of impurities and debris material from the harvested seed. Material to be removed from the seed includes but is not limited to soil, and plant waste, pebbles, weed seeds, broken soybean seeds, fungi, bacteria, insect material, including insect eggs, larvae, and parts thereof, and any other pests that exist with the harvested crop. The terms cleaning a seed or seed cleaning also refer to the removal of any debris or low quality, infested, or infected seeds and seeds of different species that are foreign to the sample.

Treating a seed or applying a treatment to a seed refers to the application of a composition to a seed as a coating or otherwise. The composition may be applied to the seed in a seed treatment at any time from harvesting of the seed to sowing of the seed. The composition may be applied using methods including but not limited to mixing in a container, mechanical application, tumbling, spraying, misting, and immersion. Thus, the composition may be applied as a powder, a crystalline, a ready-to-use, a slurry, a mist, and/or a soak. For a general discussion of techniques used to apply fungicides to seeds, see "Seed Treatment," 2d ed., (1986), edited by K A Jeffs (chapter 9), herein incorporated by reference in its entirety. The composition to be used as a seed treatment can comprise one or more of a pesticide, a fungicide, an insecticide, a nematicide, an antimicrobial, an inoculant, a growth promoter, a polymer, a flow agent, a coating, or any combination thereof. General classes or family of seed treatment agents include triazoles, anilides, pyrazoles, carboxamides, succinate dehydrogenase inhibitors (SDHI), triazolinthiones, strobilurins, amides, and anthranilic diamides. In some examples, the seed treatment comprises trifloxystrobin, azoxystrobin, metalaxyl, metalaxyl-m, mefenoxam, fludioxinil, imidacloprid, thiamethoxam, thiabendazole, ipconazole, penflufen, sedaxane, prothioconazole, picoxystrobin, penthiopyrad, pyraclastrobin, xemium, *Rhizobia* spp., *Bradyrhizobium* spp. (e.g., *B. japonicum*), *Bacillus* spp. (e.g., *B. firmus, B. pumilus, B. subtilus*), lipo-chitooligosaccharide, clothianidin, cyantraniliprole, chlorantraniliprole, abamectin, and any combination thereof. In some examples the seed treatment comprises trifloxystrobin, metalaxyl, imidacloprid, *Bacillus* spp., and any combination thereof. In some examples the seed treatment comprises picoxystrobin, penthiopyrad, cyantraniliprole, chlorantraniliprole, and any combination thereof. In some examples, the seed treatment improves seed germination under normal and/or stress environments, early stand count, vigor, yield, root formation, nodulation, and any combination thereof. In some examples seed treatment reduces seed dust levels, insect damage, pathogen establishment and/or damage, plant virus infection and/or damage, and any combination thereof.

Other non-limiting embodiments of the invention include by are not limited to:

1. A method of detecting a first soybean plant or germplasm with a maximal reproductive growth phenotype, the method comprising detecting at least one favorable allele of one or more marker locus within 30 cM of a polynucleotide selected from the group consisting of a genomic DNA region selected from the group consisting of SEQ ID NOs: 1-15;

2. The method of embodiment 1, wherein said detecting comprises detection of a haplotype comprising two or more markers within 30 cM of at least one polynucleotide selected from the group consisting of a genomic DNA region selected from the group consisting of SEQ ID NOs: 1-15;

3. The method of embodiment 1 or 2, wherein said detecting comprises detection of a haplotype comprising three or more markers selected from the group consisting of a genomic DNA region selected from the group consisting of SEQ ID NOs: 1-15;

4. The method of any one of embodiments 1-3, wherein at least one favorable allele of one or more marker loci is selected from the group consisting of S03703-1, S16601-001, and S01574-1;

5. The method of any one of embodiments 1-4 wherein detecting comprising sequencing at least one of said marker loci;

6. The method of any one of embodiments 1-5, wherein the detecting comprises amplifying the marker locus or a portion of the marker locus and detecting the resulting amplified marker amplicon.

7. The method of embodiment 6, wherein the amplifying comprises:
    a) admixing an amplification primer or amplification primer pair with a nucleic acid isolated from the first soybean plant or germplasm, wherein the primer or primer pair is complementary or partially complementary to at least a portion of the marker locus and is capable of initiating DNA polymerization by a DNA polymerase using the soybean nucleic acid as a template; and
    b) extending the primer or primer pair in a DNA polymerization reaction comprising a DNA polymerase and a template nucleic acid to generate at least one amplicon;

8. The method of embodiment 7, wherein the admixing of step 1) further comprises admixing at least one nucleic acid probe;

9. The method of any one of embodiments 1-8, wherein detecting comprises PCR analysis;

10. The method of any one of embodiments 1-5, wherein detecting comprises sequencing;

11. The method of any one of embodiments 1-10, further comprising selecting the first soybean plant or germplasm, or selecting a progeny of the first soybean plant or germplasm;

12. The method of embodiment 11, further comprising crossing the selected first soybean plant or germplasm with a second soybean plant or germplasm;

13. The method of embodiment 12, wherein the second soybean plant or germplasm comprises an exotic soybean strain or an elite soybean strain;

14. A kit for selecting at least one soybean plant, the kit comprising:
    a) primers or probes for detecting one or more marker loci of embodiment 1 associated with a preferred reproductive growth phenotype in soybean; and
    b) instructions for using the primers or probes for detecting the one or more marker loci and correlating the detected marker loci with predicted reproductive growth phenotype;

15. The kit of embodiment 14, wherein the primers or probes comprise one or more of SEQ ID NOs: 1-15;

16. The kit of any one of embodiments 14 or 15, wherein the primers or probes comprise one or more of SEQ ID NOs: 1-4, 6-9, or 11-14.

17. An isolated polynucleotide capable of detecting a polymorphism in a genomic region of soybean selected from the group consisting of an E1 locus on chromosome 6, an E2 locus on chromosome 10, and an E3 locus on chromosome 19;

18. The isolated polynucleotide of embodiment 17, wherein the polynucleotide comprises a nucleotide sequence selected from the group consisting of SEQ ID NOs: 1-15;

19. A method of soybean plant breeding comprising:
   a) crossing at least two different soybean parent plants, wherein each parent soybean plant has a known days to R1 phenotype;
   b) obtaining a population of progeny soybean seed from said cross;
   c) genotyping the progeny soybean seed with at least one genetic marker; and,
   d) selecting a subpopulation comprising at least one soybean seed possessing a genotype for decreased days to R1,
   wherein the mean days to R1 of the selected subpopulation is less than the mean days to R1 of the non-selected progeny subpopulation;

20. The method of embodiment 19 wherein the marker genotype differs between the two parents, and wherein the R1 phenotype does not differ between the two parents;

21. The method of any one of embodiments 19-20, wherein the parent soybean plants differ in days to R1;

22. The method of any one of embodiments 19-21, wherein parent soybean plants differ in days to R1 by at least 4 days.

23. A method of soybean plant breeding comprising:
   a) crossing two different soybean parent plants, wherein the parent soybean plants differ in days to R1, and the parent soybean plant is adapted for a selected growing region;
   b) obtaining progeny soybean seed from said cross;
   c) genotyping the progeny seed of said cross with a genetic marker; and,
   d) selecting progeny soybean seed possessing a genotype for decreased days to R1;

24. The method of embodiment 23, wherein the parent plants differ in maturity by at least 10 days;

25. The method of any one of embodiments 23 or 24, wherein the selected progeny soybean seed are adapted for the selected growing region;

26. The method of any one of embodiments 23-25, wherein the selected progeny soybean seed are adapted for planting as a second crop in the selected growing region;

27. The method of any one of embodiments 23-26, wherein the selected progeny have a relative maturity of 000.0 to 3.5;

28. The method of embodiment 20, wherein the selected subpopulation is adapted for a selected growing region;

29. The method of any one of embodiments 19 or 20, wherein the selected subpopulation is adapted for planting as a second crop in the selected growing region;

30. The method of any one of embodiments 19, 28, or 29, wherein the subpopulation has an average relative maturity of 000.0 to 3.5;

31. A method for extending the length of a reproductive growth stage of a soybean plant, the method comprising detecting at least one favorable allele of one or more marker locus within 30 cM of a polynucleotide selected from the group consisting of a genomic DNA region selected from the group consisting of SEQ ID NOs: 1-15; and, selecting a soybean seed or soybean plant having a genotype for decreased days to R1, wherein the soybean seed or plant has an extended length of reproductive growth.

32. The method of embodiment 31, wherein the selected soybean seed or soybean plant are adapted for a selected growing region;

33. The method of any one of embodiments 31 or 32, wherein the selected progeny soybean seed are adapted for planting as a second crop in the selected growing region;

34. The method of any one of claims 31-33, wherein the selected soybean seed or soybean plant has a relative maturity of 000.0 to 3.5;

35. The method of any one of claims 19-34, wherein of one or more marker loci is selected from the group consisting of S03703-1, S16601-001, and S01574-1;

The present invention is illustrated by the following examples. The foregoing and following description of the present invention and the various examples are not intended to be limiting of the invention but rather are illustrative thereof. Hence, it will be understood that the invention is not limited to the specific details of these examples.

EXAMPLES

Example 1

A population was developed by crossing 900Y71 with 93Y43 (900Y71/93Y43). Soybean variety 900Y71 is a maturity group (MG) 00 line while 93Y43 is a (MG) III line. This population segregates for at least two unlinked QTL/genes that govern physiological maturity. These two regions are known as E1 and E2. Historically, the E1 locus delineates ultra-early (MG 00) maturing soybean genotypes from later maturing genotypes while the E2 locus delineates MG I and earlier maturing genotypes from later maturing genotypes. In the context of the 900Y71/93Y43 population, 900Y71 contains the ultra-early allele at the E1 genetic locus, and the early allele at the E2 genetic locus. The 93Y43 line contains the early allele at the E1 locus, and the late allele at the E2 locus. 900Y71 and 93Y43 are monomorphic for a late E3 allele. Ultimately, through the utilization of molecular markers, a total of 190 plants that were identified as being fixed homozygous for the E1 and E2 loci (e.g. fixed ultra-early E1, early E2; early E1, early E2; ultra-early E1, late E2; and early E1, late E2) using the markers summarized in Table 1 below. The C allele for marker S03703-1 can also be used to detect the late allele for E1 in later maturity groups, as well as the ultra-early phenotype in the early maturity groups. Given the pedigree, genotypic characterization, and relative maturity, the C allele for marker S03703-1 is detecting the ultra-early E1 allele derived from the 900Y71 parent.

TABLE 1

| Marker | Locus | LG (ch) | Genetic (cM) | Physical (bp) | Allele polymorphism |
|---|---|---|---|---|---|
| S03703-1 | E1 | C2 (6) | 102.26 | Gm06:20084642 | C/T (ultra-early/early) |
| S01574-1 | E2 | O (10) | 99.5 | Gm10:44732850 | C/A (early/late) |

F$_3$ seed from the 190 homozygous lines was then planted in randomized 7.5-foot plots Leaf tissue from each line was collected, DNA was extracted, and the E1 and E2 molecular markers were assayed to confirm the genotype utilizing the markers in Table 1. Eighty-four lines were confirmed fixed homozygous for the E1 null allele (ultra-early phenotype), 94 lines were fixed homozygous for the E1 early allele, 68 lines were fixed homozygous for the early E2 allele, and 117 lines were fixed homozygous for the late E2 allele. Twenty-nine lines were fixed homozygous for the ultra-early E1 allele and the early E2 allele, 33 lines were fixed homozygous for the early E1 and early E2 alleles, 51 lines were fixed homozygous for the ultra-early E1 allele and late E2 allele, and 61 lines were fixed homozygous for the early E1 allele and late E2 allele.

The data collected throughout the growing season included flowering date, physiological maturity date, and plant height. The duration between flowering date and maturity date, also known as days in reproductive growth, was calculated and utilized as an additional analysis variable. Data were subjected to analysis of variance via IMP V.11 software (SAS Institute, Cary, N.C.). Separate analyses were carried out to assess the main effects of E1, E2, and as well as the four combinations of E1 and E2 have on plant height, days from planting to flowering (FLAB S), days from planting to maturity (MATABS), and the number of days from flowering to maturity (FL-MAT). Mean separation for each marker class and combinations of marker classes at each genomic region was carried out via Student's t-test at an alpha level of 0.05. These analyses are summarized in Tables 2 and 3. Table 2 summarizes the average values of the E1 alleles (ultra-early and early) for height, number of days to flowering (FLAB S), number of days to maturity (MATABS), and number of days from flowering to maturity (FL-MAT). Additionally, the effect of an allele substitution (the difference between the early allele and the ultra-early allele) and an indication of the significance between the two allele mean values are included. Table 3 summarizes the effects of the E2 alleles.

TABLE 2

|  | Ultra-early E1 Allele | Early E1 Allele | Allelic Substitution | Significant at 0.05 level |
| --- | --- | --- | --- | --- |
| Height (in) | 29.4 | 37.8 | 8.4 | Yes |
| FLABS | 37.3 | 45.0 | 7.7 | Yes |
| MATABS | 109.3 | 119.1 | 9.8 | Yes |
| FL-MAT | 72.0 | 74.1 | 2.1 | Yes |

TABLE 3

|  | Early E2 Allele | Late E2 Allele | Allelic Substitution | Significant at 0.05 level |
| --- | --- | --- | --- | --- |
| Height (in) | 29.8 | 35.9 | 6.1 | Yes |
| FLABS | 38.3 | 42.9 | 4.6 | Yes |
| MATABS | 108.8 | 117.8 | 9.0 | Yes |
| FL-MAT | 70.4 | 74.8 | 4.5 | Yes |

Table 4 below summarizes the effects for E1 and E2 alleles in combination for height, number of days to flowering (FLABS), number of days to maturity (MATABS), and number of days from flowering to maturity (FL-MAT). Letters denote significant differences among allele combinations for each phenotype (values not connected by the same letter are significantly different at the 0.05 alpha level).

TABLE 4

|  | Early E1, Early E2 | Early E1, Late E2 | Ultra-early E1, Early E2 | Ultra-early E1, Late E2 |
| --- | --- | --- | --- | --- |
| Height (in) | 33.3 B | 40.2 A | 26.3 D | 31.1 C |
| FLABS | 39.9 B | 47.8 A | 36.8 C | 37.6 C |
| MATABS | 112.1 B | 122.9 A | 104.8 C | 112.0 B |
| FL-MAT | 72.2 B | 75.1 A | 68.1 C | 74.4 A |

The early E1, early E2 class and ultra-early E1, late E2 classes were found to have a similar average for MATABS at 112.1 and 112.0 days respectively. Thus, by combining the ultra-early E1 allele (MG00 lines) with the late E2 allele (MG II and later), new lines can be created that have similar physiological maturity to a line with the early E1 allele and early E2 allele. Additionally, this novel ultra-early E1, late E2 combination has a flowering date 3.1 days earlier than the early E1, early E2 combination which translates into a greater duration of time in reproductive growth. The ultra-early E1, late E2 class spent the greatest percentage of time in reproductive growth stage at 66% as noted in Table 5.

TABLE 5

| Growth Phase | Early E1, Early E2 | Early E1, Late E2 | Ultra-early E1, Early E2 | Ultra-early E1, Late E2 |
| --- | --- | --- | --- | --- |
| Vegetative | 36% | 39% | 35% | 34% |
| Reproductive | 64% | 61% | 65% | 66% |

Example 2

A population was developed by crossing RJS06007 by 900Y61 (RJS06007/900Y61). Soybean variety RJS06007 is a (MG) 0 line while 900Y61 is a (MG) 00 line. This population segregates for at least two unlinked QTL/genes associated with physiological maturity. These two regions are known as E1 and E3, exemplary markers are shown in Table 6.

TABLE 6

| Marker | Locus | LG (ch) | Genetic (cM) | Physical (bp) | Allele polymorphism |
| --- | --- | --- | --- | --- | --- |
| S03703-1 | E1 | C2 (6) | 102.26 | Gm06:20084642 | C/T (ultra-early/early) |
| S16601-001 | E3 | L (19) | 87.73 | Gm19:47535046 | C/A (early/late) |

Historically, the E1 locus delineates ultra-early (MG 00) maturing soybean genotypes from later maturing genotypes while the E3 locus delineates MG II and earlier maturing genotypes from later maturing genotypes. In the context of the RJS06007/900Y61 population, RJS06007 contains the early E1 allele and the early E3 allele. 900Y61 contains the ultra-early allele at the E1 genetic locus, and the late allele at the E3 genetic locus. A third maturity locus, E2, is monomorphic for the early E2 allele in the parents of this population, thus does not segregate. The utilization of molecular markers associated with these loci (Table 6) revealed a total of 481 lines were fixed for homozygous for either the early or late alleles for the E1 and E3 loci. A total 93 lines were fixed homozygous for the ultra-early E1 allele, 223 lines were fixed for the early E1 allele, 221 lines were fixed for the early E3 allele, and 171 lines were fixed for the late E3 allele. With regards to the four allele combinations contained within this population, a total of 25 lines were identified as having the ultra-early E1, early E3 combination, 38 lines were found to have the ultra-early E1, late E3 combination, 41 lines had the early E1, late E3 combination, and 123 lines were identified as having the early E1, early E3 allele combination.

Lines from this RJS06007/900Y61 population were grown at environments in Northern Minnesota in 7.5-foot plots where phenotypic data on plant height, date of flowering, and date of physiological maturity were collected (half the population was grown at one environment while the remaining half was grown at another). The duration of time spent in reproductive growth was calculated as the duration of time (days) between flowering date and physiological maturity date. Leaf tissue was collected during the growing season as well for DNA extraction and the molecular marker assays.

Data from the three observed traits and one calculated trait were subjected to analysis via JMP V.11 software (SAS Institute, Cary, N.C.) where means comparisons for each allelic main effect as well as the four combinations were assessed via t-test at an alpha level of 0.05. Table 7 and 8 summarize the main effects of E1 and E3 for plant height, the number of days between planting until flowering (FLABS), the number of days between planting and physiological maturity (MATABS), and the duration between flowering and maturity (FL-MAT).

TABLE 7

|  | Ultra-early E1 | Early E1 | Allelic Substitution | Significant at 0.05 level |
|---|---|---|---|---|
| Height (in) | 26.6 | 32.3 | 5.7 | YES |
| FLABS | 43.9 | 47.5 | 3.6 | YES |
| MATABS | 112.2 | 121.7 | 9.5 | YES |
| FL-MAT | 68.3 | 74.2 | 5.9 | YES |

TABLE 8

|  | Early E3 | Late E3 | Allelic Substitution | Significant at 0.05 level |
|---|---|---|---|---|
| Height (in) | 30.0 | 32.8 | 2.8 | YES |
| FLABS | 46.0 | 45.9 | −0.1 | NO |
| MATABS | 117.8 | 121.1 | 3.3 | YES |
| FL-MAT | 71.8 | 75.2 | 3.4 | YES |

On average, plants having the ultra-early E1 allele were 5.7 inches shorter than early E1 lines; ultra-early lines flowered 3.6 days earlier, matured 9.5 says sooner, and had a 5.9 day shorter flowering to maturity duration compared to the early E1 lines (all factors were significantly different between the two alleles). Early E3 lines where on average 2.8 inches shorter, matured 3.3 days sooner, and had a flowering to maturity duration 3.4 days shorter than late E3 lines (FLAB S was not significantly different). Data shown in Table 9 indicate the average values for the four different combinations of the E1 and E3 alleles. Letters denote significant differences among allele combinations for each phenotype (values not connected by the same letter are significantly different at the 0.05 alpha level).

TABLE 9

|  | Ultra-Early E1, Early E3 | Ultra-Early E1, Late E3 | Early E1, Early E3 | Early E1, Late E3 |
|---|---|---|---|---|
| HGT | 24.9 D | 28.3 C | 31.3 B | 34.5 A |
| MATABS | 110.3 D | 113.2 C | 119.7 B | 125.5 A |
| FLABS | 43.8 C | 43.7 C | 47.0 B | 48.9 A |
| FL-MAT | 66.5 D | 69.5 C | 72.7 B | 76.6 A |

The parental combinations, ultra-early E1, late E3 (900Y61) and early E1, early E3 (RJS06007) where found to have maturity values of 113.2 and 119.7, respectively, thus a 6.5 day difference in the duration of time between planting and maturity. The early E1, late E3 class was the latest maturing combination; 5.8 days later maturing than the early E1, early E3 class. The early E1, late E3 combination is common, and phenotypic values for this class agree with previously collected data. The unique, ultra-early E1, early E3 combination matured nearly three days (2.9) earlier than the ultra-early E1, late E3 combination (900Y61 type) indicating that lines may be created in (MG) 000 and early (MG) 00 maturity segments.

Example 3

From the analyses of marker loci associated with reproductive stage in soybean populations and varieties, several markers were developed, tested, and confirmed, as summarized in preceding tables. Any methodology can be deployed to use this information, including but not limited to any one or more of sequencing or marker methods.

In one example, sample tissue, including tissue from soybean leaves or seeds can be screened with the markers using a TAQMAN® PCR assay system (Life Technologies, Grand Island, N.Y., USA).

TAQMAN® Assay Conditions
Reaction Mixture (Total Volume=5 µl):

| Genomic DNA (dried) | 16 ng |
|---|---|
| DDH2O | 2.42 µl |
| Klearkall Mastermix | 2.5 µl |
| Forward primer (100 µM) | 0.0375 µl |
| Reverse primer (100 µM) | 0.0375 µl |
| Probe 1 (100 µM) | 0.005 µl |
| Probe 2 (100 µM) | 0.005 µl |

Reaction Conditions:

| 94° C. 10 min | 1 cycle |
|---|---|

40 cycles of the following:

| 94° C. 30 sec |
|---|
| 60° C. 60 sec |

Klearkall Mastermix is available from KBioscience Ltd. (Hoddesdon, UK).

Table 10 summarizes exemplary allele polymorphisms and further associates them with early or late phenotype for time to flowering and/or maturity.

TABLE 10

| Marker | Genetic (cM) | Physical (bp) | Allele polymorphism (Early/Late) |
|---|---|---|---|
| S03703-1-Q1 | 102.26 | Gm06:20084642 | C (ultra-early)/T (early) |
| S16601-001-Q001 | 87.73 | Gm19:47535046 | C/A |
| S01574-1-A | 99.5 | Gm10:44725777 | C/A |

The SNP markers identified in these studies could be useful, for example, for detecting and/or selecting soybean plants with a preferred reproductive growth phenotype. The physical position of each SNP is provided in Table 10 based upon the JGI Glyma1 assembly (Schmutz et al. (2010) Nature 463:178-183). Any marker capable of detecting a polymorphism at one of these physical positions, or a marker associated, linked, or closely linked thereto, could also be useful, for example, for detecting and/or selecting soybean plants with an altered reproductive growth phenotype. In some examples, the SNP allele present in the first parental line could be used as a favorable allele to detect or select plants with altered time to R1, such as a shorter time to floral initiation. In other examples, the SNP allele present in the second parent line could be used as an allele to detect or select plants for unaltered time to R1.

These SNP markers could also be used to determine a preferred or non-preferred haplotype and/or marker profile. In certain examples, a favorable haplotype and/or marker profile would include any combinations of two or more of the alleles provided in Table 10. In addition to the markers listed in the Table 10, other closely linked markers could also be useful for detecting and/or selecting soybean plants with a preferred reproductive growth phenotype. For other marker loci useful to identify a preferred reproductive growth genotype and phenotype, see, for example PCT/US2014/21517 "Compositions Associated with Soybean Reproductive Growth and Methods of Use" which discloses many loci, markers, alleles, polymorphisms, chromosomal intervals, haplotypes, and/or marker profiles which can be used alone or in combination with the markers provided herein, the disclosure of PCT/US2014/21517 is herein incorporated by reference.

What is claimed is:

1. A method of producing a soybean plant comprising a marker profile associated with reproductive growth in soybean, the method comprising:

a) crossing at least one first soybean plant comprising an ultra-early allele at an E1 locus, wherein the ultra-early allele at the E1 locus is a C at Gm06:20084642, with at least a second soybean plant comprising a late allele at an E2 locus, wherein the late allele at the E2 locus is a C Gm10:44725777;

b) obtaining at least one progeny soybean plant from the cross of the at least one first soybean plant and the at least one second soybean plant;

c) assaying the progeny plant with respect to markers S03703-1 and S01574-1, as to identify if the progeny plant is homozygous for the E1 and E2 loci, respectively; and d) selecting a soybean plant or progeny thereof homozygous for the E1 and E2 loci, thus producing a soybean with a marker profile associated with reproductive growth.

2. A method of producing a soybean plant comprising a marker profile associated with reproductive growth in soybean, the method comprising:

a) crossing at least one first soybean plant comprising an ultra-early allele at an E1 locus, wherein the ultra-early allele at the E1 locus is a C at Gm06:20084642, with at least a second soybean plant comprising an early allele at an E3 locus, wherein the early allele at the E3 locus is a C Gm19:47535046;

b) obtaining at least one progeny soybean plant from the cross of the at least one first soybean plant and the at least one second soybean plant;

c) assaying the progeny plant with respect to markers S03703-1 and S16601-001, as to identify if the progeny plant is homozygous for the E1 and E3 loci, respectively; and d) selecting a soybean plant or progeny thereof homozygous for the E1 and E3 loci, thus producing a soybean with a marker profile associated with reproductive growth.

3. The method of claim 1, wherein the marker profile further comprises a late allele at the E3 locus.

4. The method of claim 2, wherein the marker profile further comprises a late allele at the E2 locus.

5. The method of any one of claims 1-4, wherein the soybean plant comprising the marker profile has a decreased time from planting to initiation of flowering.

6. The method of any one of claims 1-4, wherein the soybean plant comprising the marker profile has an increased time from initiation of flowering to full maturity.

7. The method of any one of claims 1-4, wherein the assaying comprises amplifying at least one marker locus or a portion of the marker locus and detecting a resulting amplified marker amplicon.

8. The method of any one of claims 1-4, wherein the assaying comprises sequencing.

9. The method of any one of claims 1-4, wherein the second soybean plant or germplasm comprises an exotic soybean strain or an elite soybean strain.

10. The method of any one of claims 1-4, wherein the selected soybean plant or progeny thereof are adapted for a selected growing region.

11. The method of any one of claims 1-4, wherein the selected soybean plant or progeny thereof are adapted for planting as a second crop in a selected growing region.

12. The method of any one of claims 1-4, wherein the soybean plant or progeny thereof have a relative maturity of 000.0 to 3.5.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Glycine max

<400> SEQUENCE: 1
cccaaggact aaccaggatt c                                          21

<210> SEQ ID NO 2
<211> LENGTH: 26
<212> TYPE: DNA
<213> ORGANISM: Glycine max

<400> SEQUENCE: 2
tttattaaat ggagtgagaa ggtgtc                                     26

<210> SEQ ID NO 3
<211> LENGTH: 15
<212> TYPE: DNA
<213> ORGANISM: Artificial Sequence
<220> FEATURE:
<223> OTHER INFORMATION: S03703-1 Probe1

<400> SEQUENCE: 3
acacaagtcg ctacc                                                 15

<210> SEQ ID NO 4
<211> LENGTH: 14
<212> TYPE: DNA
<213> ORGANISM: Artificial Sequence
<220> FEATURE:
<223> OTHER INFORMATION: S03703-1 Probe2

<400> SEQUENCE: 4
cacaagccgc tacc                                                  14

<210> SEQ ID NO 5
<211> LENGTH: 401
<212> TYPE: DNA
<213> ORGANISM: Glycine max

<400> SEQUENCE: 5
gttggaggat cataaaccac ttttttttgc taacaatggt attggtacaa agaagccctg    60
ccmgaagcgg tgactaatct tcgtcraaga ctatgagcat acaakagatg agtgtacgta   120
ttcccctccc aacrtgattt attcataccc aaggactaac caggattcaa acyatgaatc   180
atttgattaa gcgacamaag ycgctaccac ttgtgtcaac cgttgttrgt atcataaacc   240
acatttataa gcttaattag acaccttctc actccattta ataaattatt ttgaatatta   300 cttttttatta atatgttggt gtgaaaataa gtcaattggt cagtcgtgtc atcttattac   360
```

```
caacaagtga tttcctttag gcgactaact caagaaagaa a                  401
```

<210> SEQ ID NO 6
<211> LENGTH: 23
<212> TYPE: DNA
<213> ORGANISM: Glycine max

<400> SEQUENCE: 6

```
ttcacacatg tactaggctt tgg                                      23
```

<210> SEQ ID NO 7
<211> LENGTH: 20
<212> TYPE: DNA
<213> ORGANISM: Glycine max

<400> SEQUENCE: 7

```
ccacctttca cacagcttga                                          20
```

<210> SEQ ID NO 8
<211> LENGTH: 15
<212> TYPE: DNA
<213> ORGANISM: Artificial Sequence
<220> FEATURE:
<223> OTHER INFORMATION: S16601-001 Probe1

<400> SEQUENCE: 8

```
cagcttcaaa acatt                                               15
```

<210> SEQ ID NO 9
<211> LENGTH: 15
<212> TYPE: DNA
<213> ORGANISM: Artificial Sequence
<220> FEATURE:
<223> OTHER INFORMATION: S16601-001 Probe2

<400> SEQUENCE: 9

```
cagcttcaca acatt                                               15
```

<210> SEQ ID NO 10
<211> LENGTH: 401
<212> TYPE: DNA
<213> ORGANISM: Glycine max

<400> SEQUENCE: 10

```
caatcccaay agcctgctya aacatagaaa taaaggaatt ttatttgaaa attacttatt   60
tttcagcctt ttgaaagaag ttttgaaaaa aaaacaaact attatttctt aaaggtaatc  120
tcgtaccaaa catagttgya ttgtatctga wttcacacat gtactaggct tggcaatgc   180
tcacagtcca agcagcttca maacatttac accctgaagc atgtggcaag tcaagctgtg  240
tgaaaggtgg aatagcagtg atgttctaca catcactgtg cttgttggca ttgggaatgg  300
gaggggtgag aggatccatg actgcatttg gagctgacca atttgatgag aaggatccaa  360
ctgaggcaaa agcccttgca agttttttca attggctttt g                     401
```

<210> SEQ ID NO 11
<211> LENGTH: 22
<212> TYPE: DNA
<213> ORGANISM: Glycine max

<400> SEQUENCE: 11

```
tgaagcaact aggaaagctg aa                                       22
```

```
<210> SEQ ID NO 12
<211> LENGTH: 20
<212> TYPE: DNA
<213> ORGANISM: Glycine max

<400> SEQUENCE: 12
acgacccaat ttgcttgtct                                                 20

<210> SEQ ID NO 13
<211> LENGTH: 16
<212> TYPE: DNA
<213> ORGANISM: Artificial Sequence
<220> FEATURE:
<223> OTHER INFORMATION: S01574-1 Probe1

<400> SEQUENCE: 13
aaggcatctt tatctc                                                     16

<210> SEQ ID NO 14
<211> LENGTH: 15
<212> TYPE: DNA
<213> ORGANISM: Artificial Sequence
<220> FEATURE:
<223> OTHER INFORMATION: S01574-1 Probe2

<400> SEQUENCE: 14
aaggcatcgt tatct                                                      15

<210> SEQ ID NO 15
<211> LENGTH: 401
<212> TYPE: DNA
<213> ORGANISM: Glycine max

<400> SEQUENCE: 15
atcataatta ttgcaaaaac aatatctggt ctagtgtggg ctagataaat aagttttccc     60
tatcrgtctt tgatatcaag cctatttgag ctctcccatt cctatccaat gattttgctt    120
gatgagctct ccatatgttt tacgacccaa tttgcttgtc tctctaagaa gatmaatggc    180
atattttctt tgagagataa mgatgccttt tttggagcag gcaacttcta ttttcaggat    240 tttttttcagc tttcctagtt gcttcatttc aaattgagtt gtcaacccttt cccttaggat    300 ttgttttcaa cttcatcatt tcctgcaaca aacatatcat ctacttagac caaaaggatt    360
gccaatttac ctgtctgaaa atgctttata gagtgtggtc a                        401
```